(12) United States Patent
Fam

(10) Patent No.: US 8,382,665 B1
(45) Date of Patent: Feb. 26, 2013

(54) ENDOTRACHEAL TUBE PLACEMENT SYSTEM AND METHOD

(76) Inventor: Alfred Fam, Monroe, NJ (US)

( * ) Notice: Subject to any disclaimer, the term of this patent is extended or adjusted under 35 U.S.C. 154(b) by 136 days.

(21) Appl. No.: 12/703,537

(22) Filed: Feb. 10, 2010

Related U.S. Application Data

(60) Provisional application No. 61/151,995, filed on Feb. 12, 2009.

(51) Int. Cl.
*A61B 1/267* (2006.01)

(52) U.S. Cl. .................. 600/194; 600/120; 128/200.26

(58) Field of Classification Search .......... 600/185–200, 600/120, 122; 128/200.26
See application file for complete search history.

(56) References Cited

U.S. PATENT DOCUMENTS

| | | | | |
|---|---|---|---|---|
| 3,990,341 | A * | 11/1976 | Pace, Sr. ......................... | 84/313 |
| 4,640,273 | A * | 2/1987 | Greene et al. ................. | 128/861 |
| 4,742,819 | A | 5/1988 | George | |
| 5,329,940 | A | 7/1994 | Adair | |
| 5,607,386 | A * | 3/1997 | Flam ............................. | 600/120 |
| 5,636,625 | A | 6/1997 | Miyagi et al. | |
| 5,643,174 | A * | 7/1997 | Yamamoto et al. ........... | 600/114 |
| 5,921,917 | A | 7/1999 | Barthel et al. | |
| 5,941,816 | A | 8/1999 | Barthel et al. | |
| 5,951,463 | A | 9/1999 | Lombardi et al. | |
| 6,328,270 | B1 * | 12/2001 | Elberbaum ................. | 248/288.31 |
| 6,432,042 | B1 | 8/2002 | Bashour | |
| 6,652,453 | B2 * | 11/2003 | Smith et al. .................. | 600/188 |
| 6,743,166 | B2 | 6/2004 | Berci et al. | |
| 6,832,986 | B2 | 12/2004 | Chhibber et al. | |
| 6,929,600 | B2 | 8/2005 | Hill | |
| 2003/0195390 | A1 * | 10/2003 | Graumann ................... | 600/188 |
| 2005/0197533 | A1 | 9/2005 | May et al. | |
| 2006/0100483 | A1 | 5/2006 | Sundet et al. | |
| 2006/0247496 | A1 * | 11/2006 | Tjong Joe Wai ............. | 600/184 |
| 2007/0129603 | A1 | 6/2007 | Hirsh | |
| 2008/0236575 | A1 * | 10/2008 | Chuda ...................... | 128/200.26 |
| 2008/0312507 | A1 * | 12/2008 | Kim .............................. | 600/188 |
| 2010/0249513 | A1 * | 9/2010 | Tydlaska ...................... | 600/186 |
| 2011/0137127 | A1 * | 6/2011 | Schwartz et al. ............. | 600/188 |

\* cited by examiner

*Primary Examiner* — Jan Christopher Merene
(74) *Attorney, Agent, or Firm* — Gold & Rizvi, P.A.; H. John Rizvi

(57) ABSTRACT

An endotracheal tube placement system and method is provided including a placement-assistive handle, an oral anchor, a mechanized advancer, a video system, an endotracheal tube lock, an endotracheal tube manipulator, and an endotracheal tube stabilizer. The endotracheal tube is slipped over the endotracheal tube manipulator and is secured by the endotracheal tube lock. The placement-assistive handle houses the power supply, provides a foundation for attachment of other elements of the invention, and provides control of the tube placement. Attached to the handle is the mechanized advancer, which propels the endotracheal tube lock, endotracheal tube manipulator, and the endotracheal tube forward. The oral anchor comprises a bite block and mouth rest, and is attached to the ET supportive sheath-like ET stabilizer. The integrated video system comprises a video camera, a light source, and an LCD screen held by a swivel base.

15 Claims, 9 Drawing Sheets

FIG. 5
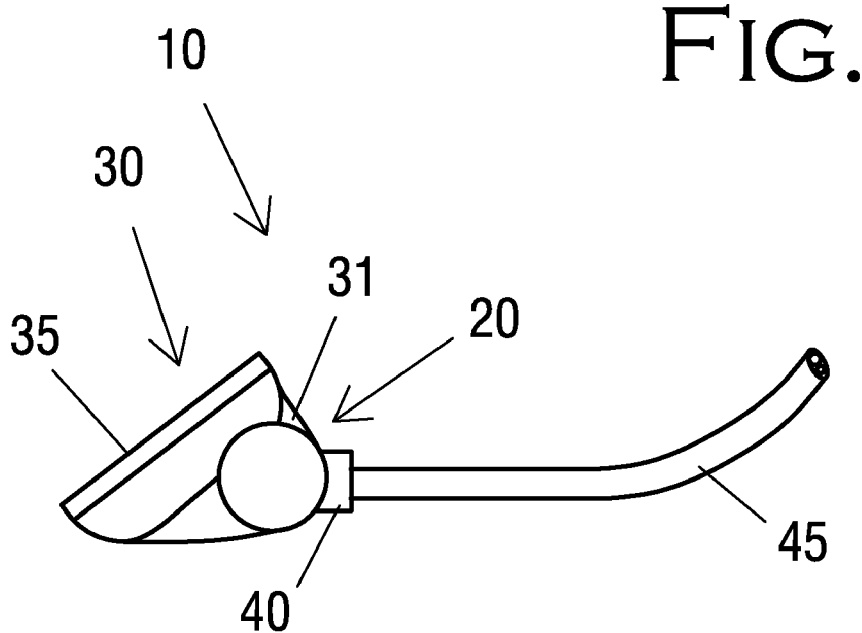
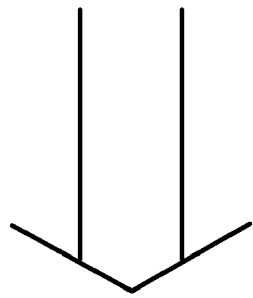
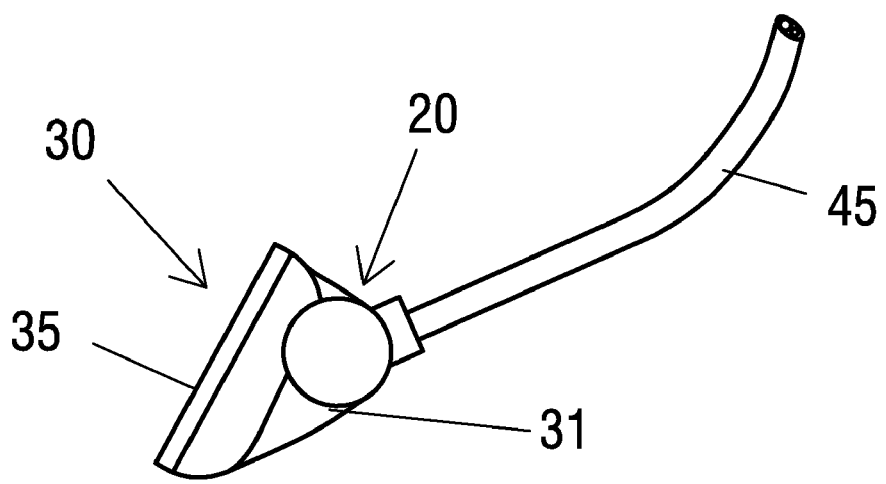

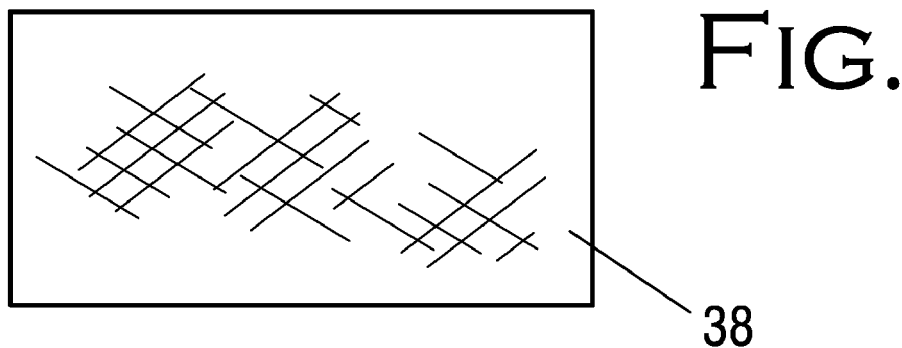
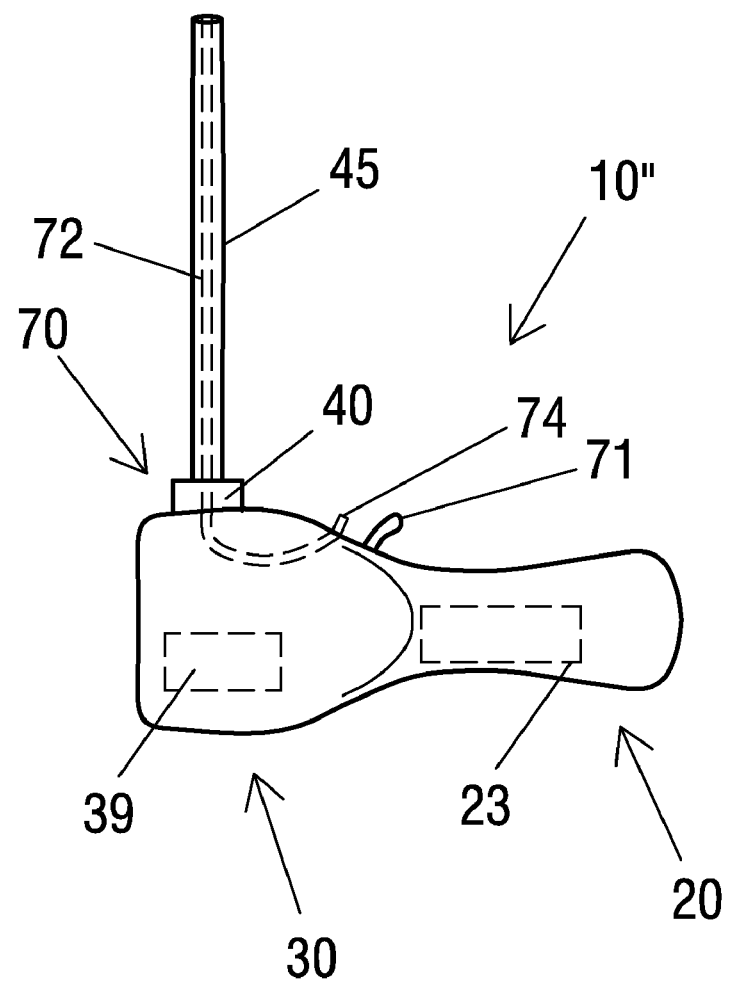
FIG. 9

ENDOTRACHEAL TUBE PLACEMENT SYSTEM AND METHOD

CROSS-REFERENCE TO RELATED APPLICATION

This Non-Provisional Patent Application claims the benefit of U.S. Provisional Patent Application Ser. No. 61/151,995, filed on Feb. 12, 2009, which is incorporated herein in its entirety.

BACKGROUND OF THE INVENTION

1. Field of the Invention

The present invention relates generally to a medical device utilized in endotracheal intubation, and more particularly, to an endotracheal tube placement system and method, including a placement-assistive handle, an oral anchor, mechanized advancer, and an integrated video viewing system allowing simultaneous visualization of the airway without a direct line of sight and introduction of the endotracheal tube.

2. Description of the Prior Art

Successful management of a patient's airway is vital. The clinician must combine quick, accurate decisions and proficient procedural skills with the proper equipment to achieve this goal. Often intubation with an endotracheal tube is required.

Standard intubation uses the direct laryngoscopy technique with a blade, such as a curved Macintosh blade. After positioning the patient's head and upper body to align the oral, pharyngeal, and laryngeal axes, the handle of the blade is held in the left hand, with the right hand used to open the mouth. The blade is inserted to the right of the tongue. When the blade approaches the base of the tongue, some traction is exerted along the long axis of the laryngoscope handle to compress the tongue, improving the ability to see the epiglottis. The tip of the blade is advanced, centered, and seated in the vallecula (the space at the junction of the base of the tongue and the origin of the epiglottis) with additional lift applied along the longitudinal axis of the laryngoscope handle to further compress the tongue and to help lift the epiglottis to reveal the vocal cords beneath.

Standard direct laryngoscopy presents a variety of problems. Care must be taken not to damage the patient's upper teeth with the laryngoscope, while attempting to attain a better view. Cervical spine injury, poor neck mobility, limited jaw opening, prominent upper teeth, and other anatomic or pathologic conditions may make standard direct laryngoscopy difficult. The manipulation of the airway increases airway trauma, as does one or more failed intubation attempts to access the trachea. Advantageously, the endotracheal tube placement system of the present invention requires less manipulation, of the airway. The decrease in manipulation reduces airway trauma, edema, and secretions, resulting in a faster recovery and extubation. Further, the endotracheal tube placement system of the present invention provides protection for the patient's teeth and saves time by eliminating the time needed to align the oral, pharyngeal, and laryngeal axes.

Direct laryngoscopy has a considerable learning curve, with studies showing best results are achieved after about 50 direct laryngoscope procedures are completed. Due to the difficulty in performing the procedure without considerable practice, laryngoscopy is generally limited to experienced laryngoscopists or anesthesiologists. Advantageously, the ease of use of the endotracheal tube placement system of the present invention allows any medical professional to intubate a patient when needed.

Although alternative intubation devices are available that may permit easier tracheal intubation in some patients who present significant difficulty with direct laryngoscopy, the endotracheal tube placement system of the present invention provides significant advantages over currently available alternative intubation devices, also.

In many of these currently available alternative intubation procedures the device is inserted, carefully advanced past the oropharynx, epiglottis, and vocal cords into the trachea, and then the endotracheal tube is introduced, with the device then removed. Advantageously, the endotracheal tube placement system of the present invention saves time in establishing an airway, as the endotracheal tube is introduced simultaneously as the airway is visualized.

Other alternative intubation procedures do not allow visualization of the intubation area. For example, a lightwand, such as the Trachlight, is a flexible wand with a distal light and retractable internal wire stylet that attaches to a handle with the correct placement of the end of the endotracheal tube confirmed by soft tissue transillumination in the neck, with the clinician seeing a circumscribed glow at the neck front from the distal light. The lightwand is a blind technique, and lacks the ease of use and visualization of the intubation area provided by the present invention.

When direct visualization of the vocal cords is limited or unattainable during standard direct laryngoscopy, some other alternative intubation devices and procedures allow indirect visualization of, the vocal cords, such as, for example, flexible fiberoptic laryngoscopy and video laryngoscopy.

A fiberoptic scope has a proximal eyepiece and a semi-malleable stylet carrying an endotracheal tube. The fiberoptic scope is inserted over or beside the tongue and advanced past the epiglottis and through the vocal cords. The endotracheal tube can then be further advanced off the stylet down the trachea. While the endotracheal tube is introduced while indirectly viewing the laryngeal area, the manipulation of the fiberoptic scope during placement is not easy or intuitive. Additionally, some fiberoptic scopes do not have integrated suction, so blood and secretions will make use of the fiberoptic scope difficult. The endotracheal tube placement system of the present invention provides an integrated suction option and allows intuitive, straightforward movements of the wrist of the clinician to manipulate and to position the endotracheal tube carried by the manipulator.

Indirect visualization of the vocal cords can also be obtained by using a video laryngoscope. Video laryngoscopy uses video technology with a camera located near the distal end of a rigid blade and a display device, such as a video monitor, to display the view at the distal end of the blade.

Video laryngoscopes are conventionally available in two varieties, one in which an adapter is used to attach a video camera to the eyepiece of a conventional fiberoptic device, and another in which the video technology is integrated into the laryngoscope, such as the video laryngoscope sold under the trademark Glidescope. The integrated video laryngoscope generally is composed of a plastic, one-piece blade and handle, with a miniature video camera and light-emitting diode (LED) light source toward its distal end. A cable, allowing transmission of the image obtained, connects the video camera to a liquid-crystal display (LCD) color monitor. Once the laryngeal inlet has been visualized, the clinician guides a stylet carrying an endotracheal tube toward and through the vocal cords. While the video laryngoscope is useful in difficult intubations to view the larynx, the procedure learning curve is challenging. Further, the additional step of guiding the styletted endotracheal tube toward and through the vocal cords, after positioning the video laryngoscope, increases the time required for the vital procedure, delaying oxygenation. Advantageously, the endotracheal tube placement system of the present invention allows simultaneous indirect visualization of the airway and introduction of an endotracheal tube, saving valuable time during an emergency in which securing an airway is the beginning step in resuscitation.

Further, some conventional fiberoptic scopes and video assisted laryngoscopes are bulky and/or complicated. The handheld endotracheal tube placement system of the present invention is self-contained, battery operated, and portable; therefore, the endotracheal tube placement system of the present invention is available in any situation. Easy disassembly of parts allows for easy storage into a portable carrying case, thus enhancing convenience, especially for transport and use by emergency personnel and for storage.

Additionally, with the conventionally available endotracheal tube placement systems, the guidance and manipulation of the endotracheal tube tip is difficult. The endotracheal tube placement system of the present invention provides a placement-assistive handle facilitating easy manipulation of the endotracheal tube tip toward any direction: Using simple, intuitive wrist movement, the endotracheal tube tip will move where desired. This gives greater control and precision, ultimately saving valuable time.

Accordingly, there is an established need for a convenient, compact, self-contained endotracheal tube placement system that has a less challenging learning curve; that allows a clinician to simultaneously indirectly view the laryngeal area as the endotracheal tube is being properly placed in position; that allows the tip of the endotracheal tube to be easily guided and manipulated with a simple wrist movement; and that minimizes airway trauma through decreased manipulation of the airway, resulting in a faster recovery and extubation.

SUMMARY OF THE INVENTION

The present invention is directed to a compact, self-contained, efficient, endotracheal tube placement system that allows the clinician to use intuitive, straightforward movements of a placement-assistive handle to intubate the patient.

The endotracheal tube placement system and method presented includes the placement-assistive handle, an oral anchor, a mechanized advancer, an integrated video system, an endotracheal tube lock, an endotracheal tube manipulator, and an endotracheal tube stabilizer.

The endotracheal tube to be used is slipped over the endotracheal tube manipulator and is secured by the endotracheal tube lock. The oral anchor comprises a bite block and mouth rest, and is attached to the supportive sheath-like endotracheal tube stabilizer.

The placement-assistive handle houses the power supply, provides a foundation for attachment of other elements of the invention, and provides control of the tube placement. Attached to the handle is the mechanized advancer, which propels the endotracheal tube lock, endotracheal tube manipulator, and the endotracheal tube forward until the endotracheal tube is in the proper position. Then the endotracheal tube and oral anchor remain in position while the endotracheal tube lock and endotracheal tube manipulator are removed.

The integrated video system comprises a video camera, a light source, and a local display screen (such as an LCD screen) held by a swivel base allowing 360 degree swivel movement. The integrated video system allows the clinician a dependable and consistent view of the area at the distal end of the endotracheal tube being positioned.

An object of the present invention is to present an endotracheal tube placement system that provides easy manipulation and guidance of the endotracheal tube tip towards any direction by using simple, intuitive wrist movements.

Another object of the present invention is to present an endotracheal tube placement system that saves valuable time in during intubation.

A further object of the present invention is to present an endotracheal tube placement system that provides greater and more precise control of the endotracheal tube tip.

An additional object of the present invention is to present an endotracheal tube placement system that allows simultaneous indirect visualization of the airway and introduction of the endotracheal tube.

Another object of the present invention is to present an endotracheal tube placement system that is compact, portable, and self-contained.

A further object of the present invention is to present an endotracheal tube placement system that has a less challenging learning curve than direct laryngoscopy.

An additional object of the present invention is to present an endotracheal tube placement system that allows a wider variety of medical professionals to intubate a patient when needed, without requiring an experienced laryngoscopist or anesthesiologist.

Another object of the present invention is to present an endotracheal tube placement system that permits easier tracheal intubation in patients who present significant difficulty with direct laryngoscopy.

An additional object of the present invention is to present an endotracheal tube placement system that minimizes airway trauma through decreased manipulation of the airway, resulting in a faster recovery and extubation.

Another object of the present invention is to present an endotracheal tube placement system that optionally provides an integrated suction system.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 5 is a right side view showing the first embodiment of the endotracheal tube placement system with a placement-assistive handle and an integrated video system of the present invention illustrating the position change of the endotracheal tube by a movement of the wrist in the y direction;

FIG. 9 is a top view showing a third embodiment of the endotracheal tube placement system and method of the present invention, illustrating an optional suction system and a large remote display screen.

Like reference numerals refer to like parts throughout the several views of the drawings.

DETAILED DESCRIPTION OF THE PREFERRED EMBODIMENTS

Figure 1:
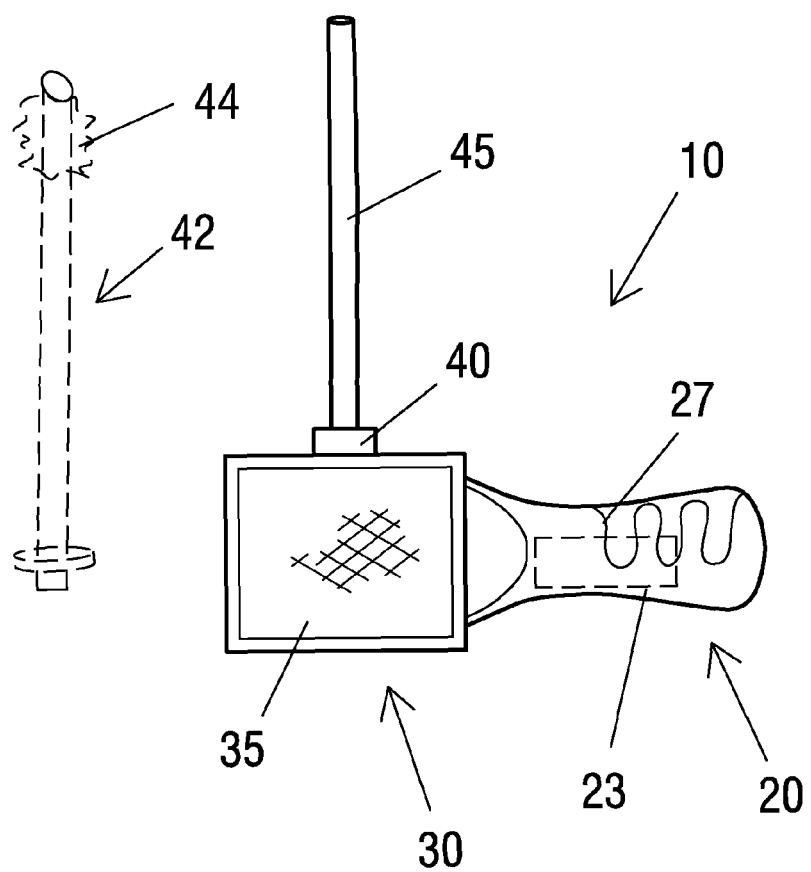
FIG. 1 is a top view showing a first embodiment of the endotracheal tube placement system with a placement-assistive handle and an integrated video system of the present invention illustrating the sliding of the endotracheal tube over the manipulator.

Shown throughout the figures, the present invention is directed toward an endotracheal tube placement system and method, including a placement-assistive handle and an integrated video viewing system, with other optional aspects including an oral anchor, an advancement halting system (including a pressure sensor), a stylet/endotracheal tube articulator, and a mechanized advancer.

The endotracheal tube placement system of the present invention saves valuable time during intubation; allows easier and more precise manipulation and guidance of the endotracheal tube tip towards any direction by using simple, intuitive wrist movements; allows simultaneous indirect visualization of the airway and introduction of the endotracheal tube; provides a compact, self-contained device that is easy to transport and assemble; reduces the learning curve of conventional direct laryngoscopy allowing intubation by a wider variety of medical professionals; minimizes airway trauma through decreased manipulation of the airway, resulting in a faster recovery and extubation; optionally provides an integrated suction system; optionally provides an advancement halting system; and optionally provides a stylet/endotracheal tube articulator.

The endotracheal tube placement system of the present invention, shown generally as reference number 10, is presented in three embodiments. The first embodiment of the endotracheal tube placement system and method, shown in FIG. 1-FIG. 6 comprises a placement-assistive handle 20, a video system 30, an endotracheal tube lock 40, and an endotracheal tube manipulator 45. The second embodiment of the endotracheal tube placement system and method, shown in FIG. 7-FIG. 8 further comprises an oral anchor 50, a mechanized advancer 60, and an endotracheal tube stabilizer and presents an optional advancement halting system (including pressure sensor 61 and advancement controller 63) and an optional stylet/tube articulator 64. The third exemplary embodiment of FIG. 9 further comprises an optional suction system 70 and a wireless video transmission system.

Figure 2:
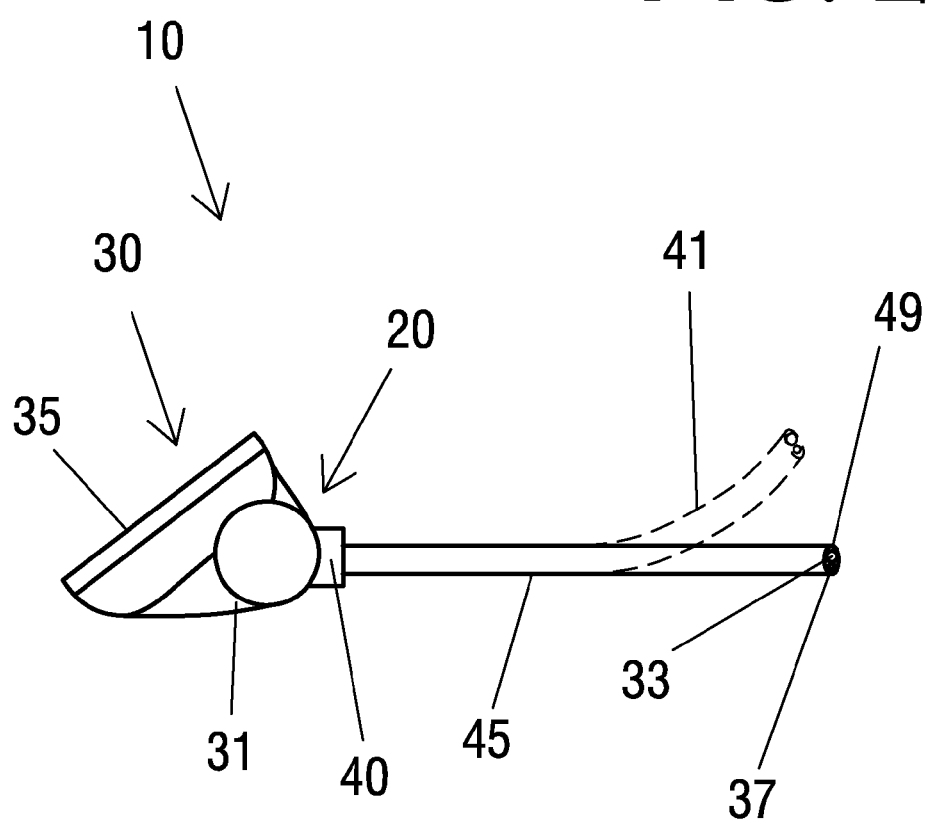
FIG. 2 is a right side view showing the first embodiment of the endotracheal tube placement system with a placement-assistive handle and an integrated video system of the present invention.
Figure 3:
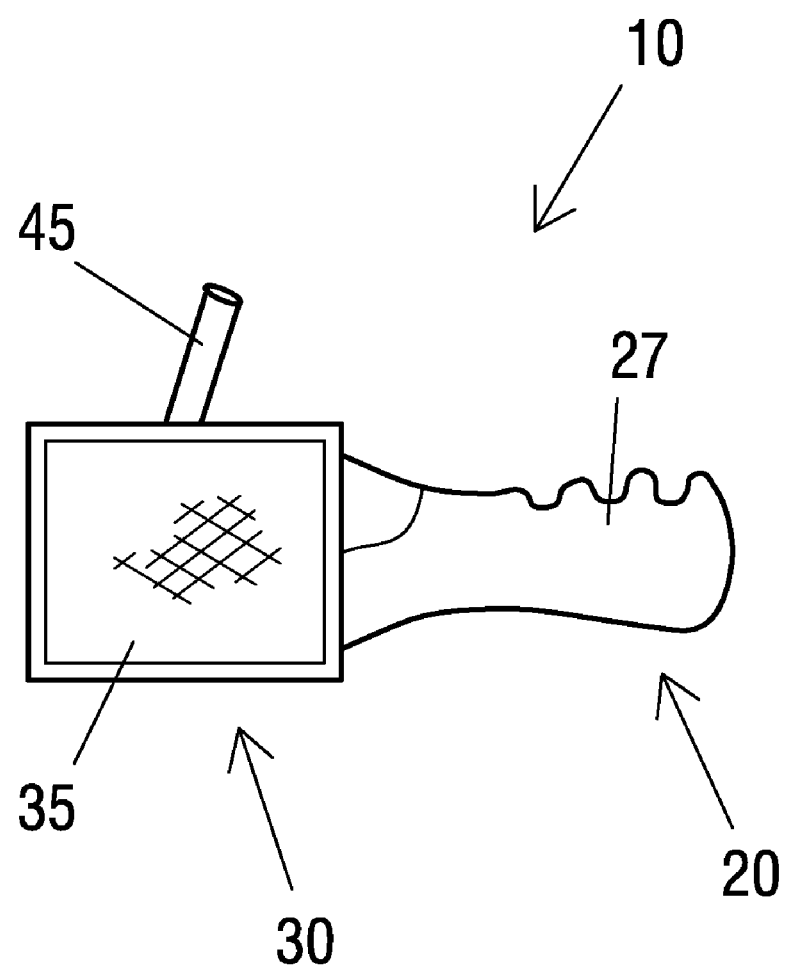
FIG. 3 is a back view showing the first embodiment of the endotracheal tube placement system with a placement-assistive handle and an integrated video system of the present invention with the local display screen rotated on the swivel base from the display screen position in FIG. 1.

Referring now to FIG. 1, FIG. 2, and FIG. 3, a top view, right side view, and back view, respectively, of the first embodiment of the endotracheal tube placement system 10 of the present invention is illustrated. A conventional endotracheal tube 42 is used with the endotracheal tube placement system 10 of the present invention during the intubation.

The placement-assistive handle 20 is a preferably ergonomically shaped handgrip that is sized and configured for comfortable manual utilization by the clinician who is performing the intubation. By controlling and moving the placement-assistive handle 20, using intuitive wrist movements, the clinician achieves control of the movement of the tip of the endotracheal tube 42, and thereby, placement of the endotracheal tube 42. The placement-assistive handle 20 preferably houses the internal power supply 23 and provides a foundation for attachment of other elements of the invention. Placement-assistive handle 20 may be formed with outer end indentations 27 configured and shaped to allow a more ergonomic fit for the hand of the clinician.

The video system 30 allows indirect visualization of the airway area near the tip of the endotracheal tube 42 during intubation, as it advances past the oropharynx, epiglottis, and vocal cords and into the trachea. The integrated video system 30 comprises a video camera 33 operatively connected to a local display screen 35 (such as a conventional LCD screen) located on a swivel base 31 and a light source 37. The swivel base 31 allows the clinician to conveniently rotate and to view the local display screen even as the endotracheal tube placement system 10 is moved during use. Swivel base 31 is attached to the inner end of placement-assistive handle 20. Preferably the swivel base 31 is a ball-in-socket type base that allows for approximately a 360 degree swivel.

The light source 37 and the video camera 33 are disposed at the distal end of endotracheal tube manipulator 45, forming an endotracheal tube eye 49, from which the image is obtained. The integrated video system 30 also comprises transmission connections to transmit the image from the distal end of endotracheal tube manipulator 45 to the display screen 35. The transmission connections may provide wired or wireless connectivity. The video system 30 allows the clinician a dependable and consistent view of the area at the distal end of endotracheal tube 42, facilitating placement in the proper location.

The endotracheal tube manipulator 45 comprises a semi-rigid, semi-malleable tube or stylet that is configured to house the video camera 33 and the light source 37. The endotracheal tube manipulator 45 is disposed at a generally right angle to placement-assistive handle 20. The endotracheal tube manipulator 45 is configured to be manually bent or manipulated by the clinician to conform to any desired shape, such as a distal upward curvature 41, as may be dictated by the patient's anatomy. The endotracheal tube manipulator 45 is configured to receive the conventional endotracheal tube 42, which is slipped on the endotracheal tube manipulator 45 prior to use of the endotracheal tube placement system 10.

Upon placement of the endotracheal tube 42 on the endotracheal tube manipulator 45 the clinician then engages the endotracheal tube 42 with the endotracheal tube lock 40. The endotracheal tube lock 40 is disposed on placement-assistive handle 20 at the proximal end of endotracheal tube manipulator 45. It is configured to secure the proximal end of endotracheal tube 42 during endotracheal tube 42 positioning and to release the endqtracheal tube 42 when it is properly positioned in the airway. Thus the endotracheal tube lock 40 holds the tube in place securely, not allowing any separation until released. After releasing, the endotracheal tube manipulator 45 is withdrawn, leaving the endotracheal tube 42 in position.

The placement-assistive handle 20 is configured to contain the internal power supply 23. Internal power supply 23 is configured to power the display screen, camera, and light source.

The placement-assistive handle 20 is preferably configured to allow the attachment of the other components of the endotracheal tube placement system 10. Preferably the local display screen 35 and the endotracheal tube manipulator 45 (with endotracheal tube eye 49) are removably attachable to the placement-assistive handle 20. The endotracheal tube manipulator 45 is preferably attachable through the endotracheal tube lock 40. This permits the disassembly of the components for easy storage. An optional portable carrying case is preferably provided for the components of the endotracheal tube placement system 10 of the present invention.

Figure 4:
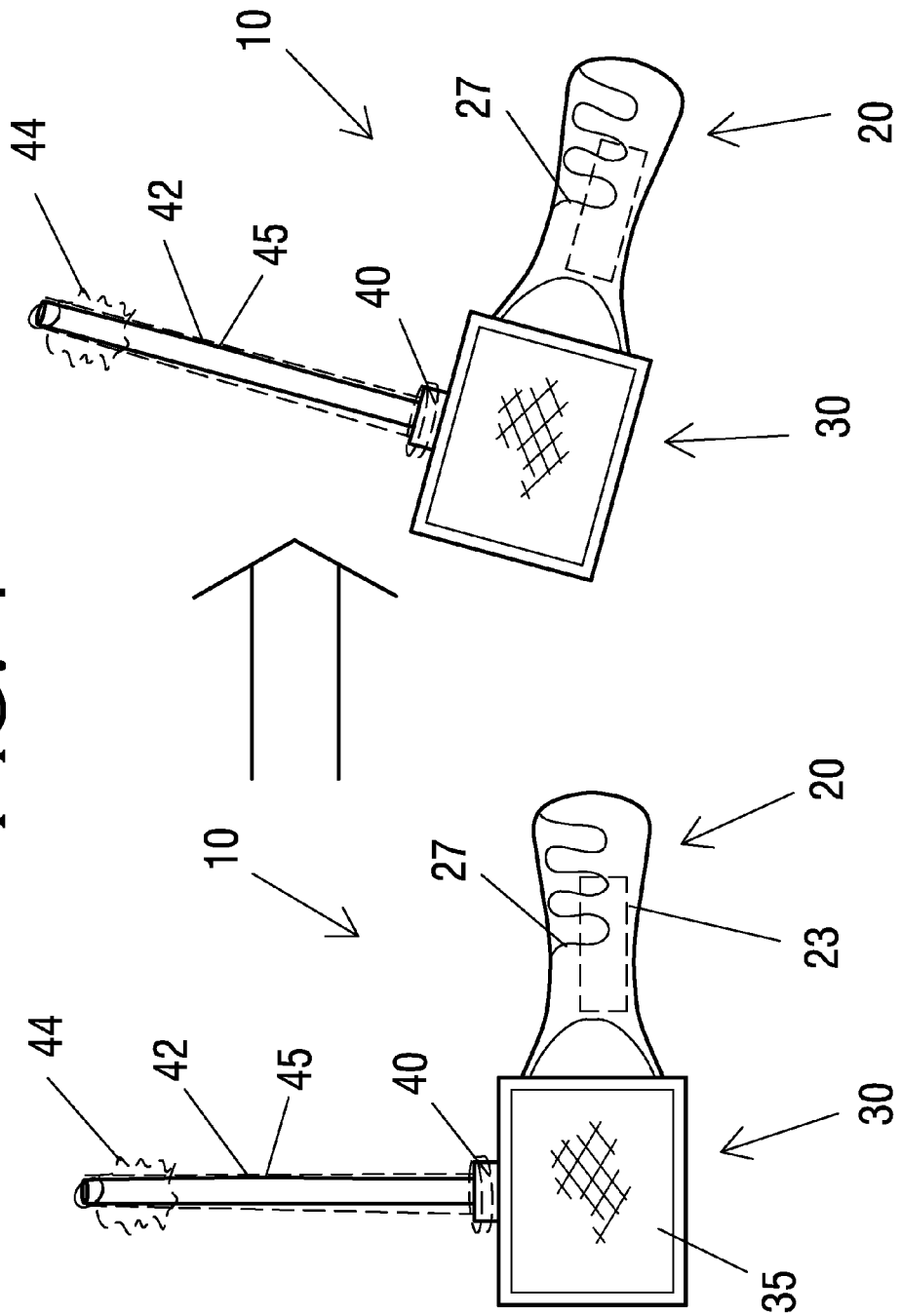
FIG. 4 is a top view showing the first embodiment of the endotracheal tube placement system with a placement-assistive handle and an integrated video system of the present invention illustrating the position change of the endotracheal tube by a right movement of the wrist.
Figure 6:
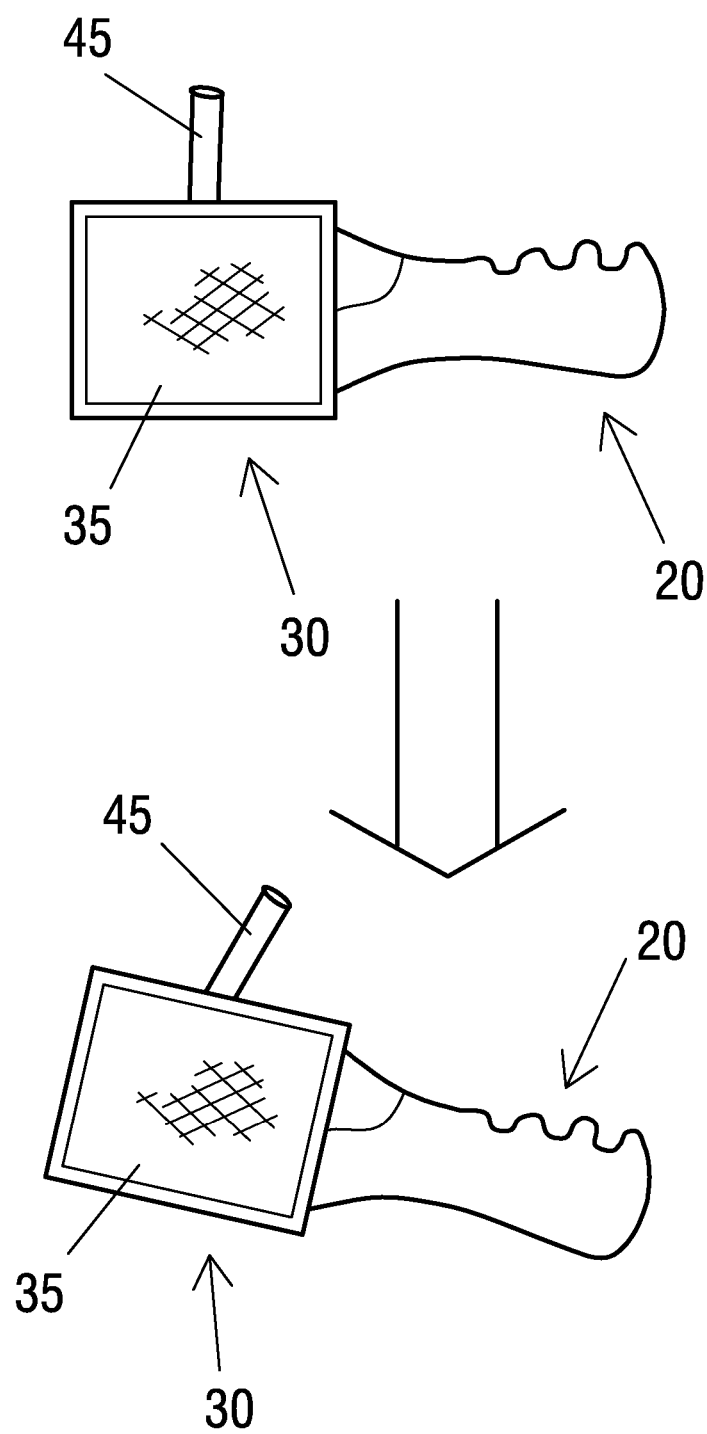
FIG. 6 is a back side view showing the first embodiment of the endotracheal tube placement system with a placement-assistive handle and an integrated video system of the present invention illustrating the position change of the endotracheal tube by a movement of the wrist in the x direction.

Illustrated in FIG. 4, FIG. 5, and FIG. 6 is the movement of the wrist of the clinician in the right/left direction (z), y direction, and x direction, respectively, facilitating the placement of the endotracheal tube 42 into the proper position by use of the placement-assistive handle 20. Further, a pushing or pulling motion (not shown) of the whole arm while holding the handle advances or retracts, respectively, the endotracheal tube placement system 10 of the present invention and with it the endotracheal tube 42.

FIG. 4 illustrates the movement in the z direction of the placement-assistive handle 20. A right to left motion of the wrist is performed, similar to the motion of waving goodbye left to right, while the arm is fixed in place, or comparable to the movement the wrist makes while casting a fishing line.

FIG. 5 illustrates the wrist movement in the y direction, flexion and extension of the wrist resulting in an up and down movement of the endotracheal tube tip. The extension of the wrist (like revving up a motorcycle engine) moves the endotracheal tube manipulator 45 upward; conversely with the flexion of the wrist (like the wrist movement of shooting a basketball) moving the distal tip of the endotracheal tube manipulator 45 downward.

FIG. 6 illustrates the wrist movement in the x direction. While firmly gripping the placement-assistive handle 20, the supination and pronation of the wrist will result in left and right movement of the endotracheal tube tip. The supination of the wrist (like the wrist movement of turning a key to the right) moves the distal tip of endotracheal tube manipulator 45 right; conversely with the pronation of the wrist (like the wrist movement of turning a key to the left) moving the distal tip of the endotracheal tube manipulator 45 left.

The simple intuitive movements of the wrist provide control of the positioning and placement of the endotracheal tube 42. The device becomes an extension of the wrist, allowing the fine control which is needed to execute the task of endotracheal intubation.

The assembly and preparation of the endotracheal tube placement 10 system of the present invention include the following steps:

Screwing the endotracheal tube manipulator 45 onto the placement-assistive handle 20;

2. Bending the semi-malleable endotracheal tube manipulator 45 to the desired angle to best suit the patient;

3. Sliding the endotracheal tube 42 over the endotracheal tube manipulator 45; and 4. Locking the endotracheal tube 42 to the endotracheal tube lock 40.

The procedure to use the endotracheal tube placement system 10 of the present invention generally includes the following steps:

Placing the patient in the supine position.

Opening the patient's mouth.

Retracting the tongue to expose the oropharynx. As minimal force is required, as opposed to standard direct laryngoscopy where the vocal cords are being visualized, any type of tongue retractor can be utilized, including, for example, a simple plastic tongue retractor or a standard laryngoscope.

Grasping the placement-assistive handle 20 handle firmly.

Introducing the endotracheal tube 42 carried by the endotracheal tube manipulator 45 into the patient's mouth.

Viewing the display screen providing indirect visualization available of the endotracheal tube 42 tip.

Moving the wrist and hand to produce movements x, y, and/or z to guide the endotracheal tube manipulator 45 carrying the endotracheal tube 42.

Positioning the endotracheal tube manipulator 45 carrying the endotracheal tube 42 in the appropriate position in the patient's airway.

Using the pushing movement of the pushing and pulling movement to advance the endotracheal tube 42 into the desired position.

Removing the tongue retractor.

Inflating the endotracheal tube 42 cuff 44.

Unlocking the endotracheal tube 42 from the endotracheal tube lock 40.

Holding the endotracheal tube 42 in place.

Pulling the endotracheal tube manipulator 45 out of the endotracheal tube 42.

Figure 7:
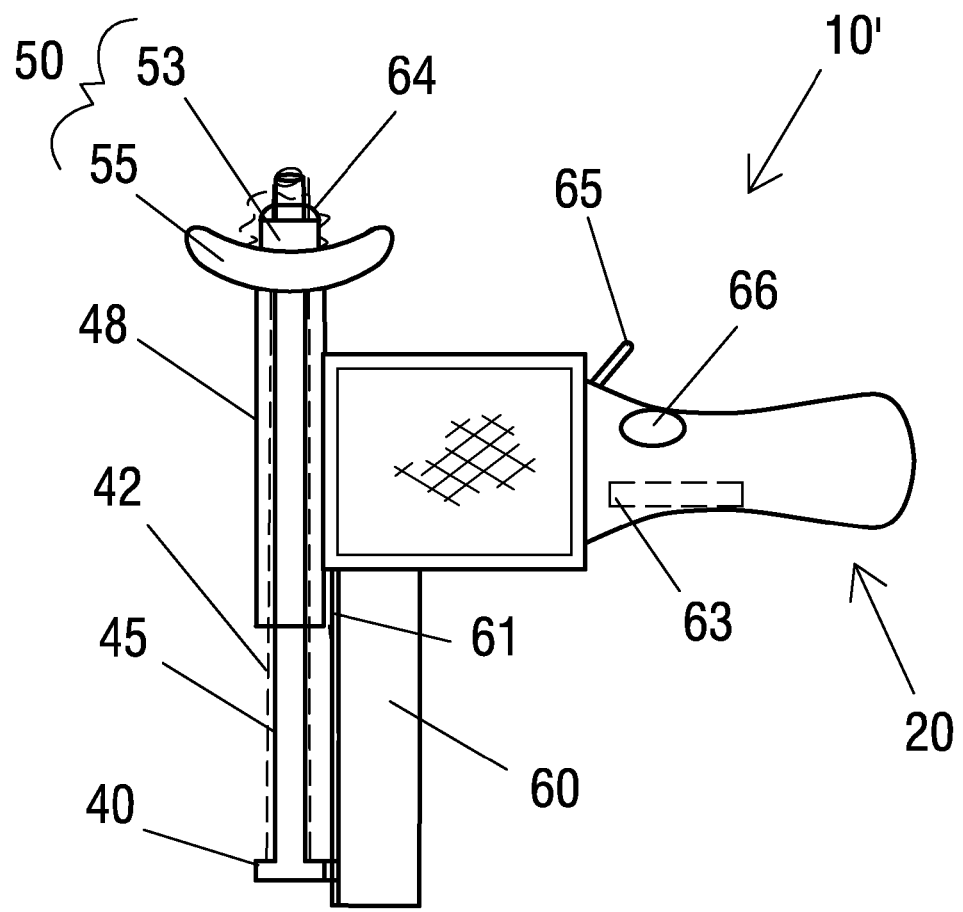
FIG. 7 is a top view showing a second embodiment of the endotracheal tube placement system and method, including a placement-assistive handle, an oral anchor, a mechanized advancer, an integrated video viewing system, and optional pressure sensor of the present invention, illustrating an un-extended endotracheal tube and endotracheal tube manipulator.
Figure 8:
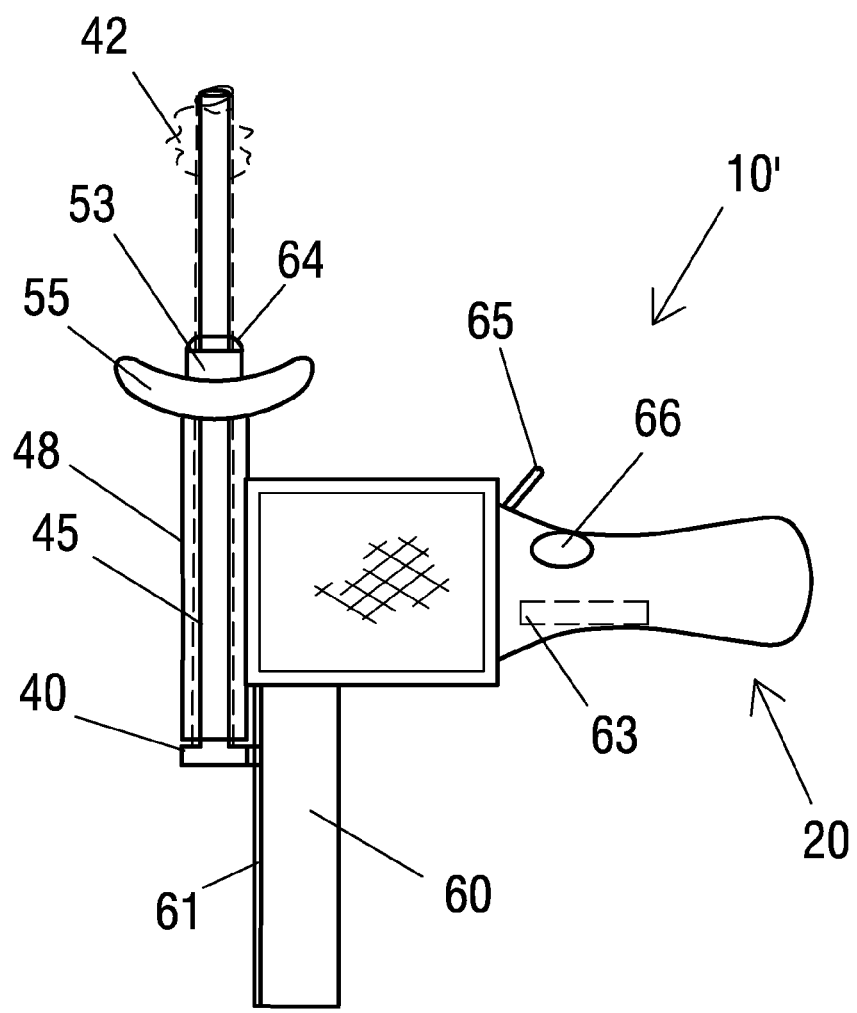
FIG. 8 is a top view showing the second embodiment of the endotracheal tube placement system and method, including a placement-assistive handle, an oral anchor, a mechanized advancer, an integrated video viewing system, and optional pressure sensor of the present invention, illustrating an extended endotracheal tube and endotracheal tube manipulator.

FIG. 7 and FIG. 8 illustrate a second exemplary embodiment of the endotracheal tube placement system of the present invention, generally referred to by the reference numeral 10'. The endotracheal tube placement system 10' is functionally similar to the first exemplary embodiment of FIG. 1 to FIG. 6, but provides additional components to facilitate intubation. The endotracheal tube placement system 10' also comprises an oral anchor 50, an endotracheal tube advancing system including a mechanized advancer 60, and an endotracheal tube stabilizer 48. Further, the endotracheal tube placement system 10' of the second embodiment presents an optional advancement halting system (which includes pressure sensor 61 and an advancement controller 63) and an optional stylet/tube articulator 64, which may provide additional performance enhancements in some situations. In most other aspects, the endotracheal tube placement system 10' is substantially similar to the endotracheal tube placement system 10 of the first embodiment described above.

The endotracheal tube advancing system comprises the mechanized advancer 60, the endotracheal tube stabilizer 48, the advancer trigger 65, the optional advancement halting system (utilizing pressure sensor 61 and advancement controller 63) and the optional stylet/tube articulator 64.

The mechanized advancer 60 is operational to advance the endotracheal tube manipulator 45 carrying the endotracheal tube 42. The mechanized advancer 60 is fixed to the placement-assistive handle 20 and directly attached to the endotracheal tube lock 40. The mechanized advancer 60 can be either motorized or mechanical, such as a crank-type mechanism.

Advancer trigger 65 is operatively connected, either mechanically or electronically, to the mechanized advancer 60. The mechanized advancer 60 is controlled by the clinician by means of the advancer trigger 65.

The endotracheal tube stabilizer 48 is preferably manufactured of a rigid material, such as a metal or a plastic or a combination of one or more metals and/or plastics. The endotracheal tube stabilizer 48 is supported by the placement-assistive handle 20 (either fixedly or removably attached). The endotracheal tube stabilizer 48 is configured as a hollow tube-like supportive sheath, sized to allow the endotracheal tube manipulator 45 carrying the endotracheal tube 42 to progress through it, upon engagement of the advancer trigger 65 by the clinician. The advancer trigger 65 is operative to prompt the mechanized advancer 60 to propel forward the endotracheal tube lock 40 and the endotracheal tube manipulator 45 carrying the endotracheal tube 42 through the tube stabilizer 48 and forward of the oral anchor 50.

The oral anchor 50 (FIG. 7) comprises a bite block 53 and a mouth rest 55. The bite block 53 and mouth rest 55 are attached to endotracheal tube stabilizer 48. The bite block 53 and mouth rest 55 are preferably made out of semi-rigid plastic that is coated with a soft rubberized material to prevent injury to the patient's teeth, gums, and/or lips.

The advancement halting system includes pressure sensor 61 and advancement controller 63. The pressure sensor 61 is adapted to sense the pressure at the distal end of the endotracheal tube manipulator. The pressure sensor 61 is operatively connected to the advancement controller 63 which is configured to halt the advancement of the mechanized advancer 60 upon receipt of an unsatisfactory reading from the pressure sensor 61. Thus if any resistance is met when the endotracheal tube is being advanced (for example, if the tube is caught on the epiglottis) this increase in pressure is identified by pressure sensor 61 and the advancement controller 63 will stop the advancement of the tube, thereby avoiding possible injury to airway structures. This will allow for repositioning with smooth advancement without a possibility for injuring airway structures.

The articulation system comprises a stylet/tube articulator and an articulation actuator. The stylet/tube articulator is adapted to increase the angle of the endotracheal tube manipulator 45 (and thus the carried tube 42) when the articulation actuator is manually engaged or depressed by the clinician. The articulation actuator is disposed on the placement-assistive handle and is configured to allow the clinician to manually articulate the stylet/tube articulator.

The procedure to assemble and use second embodiment of the endotracheal tube placement system 10' of the endotracheal tube placement system 10 of the present invention generally includes the following steps:

Attaching the endotracheal tube manipulator 45 onto the placement-assistive handle 20.

Bending the semi-malleable endotracheal tube manipulator 45 to the desired angle to best suit the patient.

Sliding the endotracheal tube 42 through the endotracheal tube stabilizer 48 and over the endotracheal tube manipulator 45, whereby only the tip of the endotracheal tube 42 projects out of the bite block 53.

Locking the endotracheal tube 42 to the endotracheal tube lock 40.

Placing the patient in the supine position.

Opening the patient's mouth.

Retracting the tongue with a tongue retractor to expose the oropharynx.

Grasping the placement-assistive handle 20 handle firmly.

Introducing the endotracheal tube 42 tip and bite block 53 into the patient's mouth. At this point the bite block and endotracheal tube will not advance past what the mouth rest will allow, as the mouth rest is shaped like a pacifier that sits over the lips. Because the mouth rest and bite block are resting on the patients mouth, this takes advantage of the patients own anatomy (the upper and lower jaws) and uses them as anchors to help stabilize the movements. This creates a "tripod" effect because the semi-rigid nature of the mouth rest allows for movement in any direction.

Viewing the display screen providing indirect visualization available of the endotracheal tube 42 tip.

Moving the wrist and hand to produce movements x, y, and/or z to direct the endotracheal tube manipulator 45 (carrying the endotracheal tube 42) into the proper direction.

Pressing the advancer trigger 65 to advance the endotracheal tube manipulator 45 (carrying the endotracheal tube 42), so as to facilitate deployment of the endotracheal tube 42 and manipulator 45 through the mouth into the oropharynx.

Continuing to move the wrist and hand to produce movements x, y, and/or z to direct the endotracheal tube manipulator 45 (carrying the endotracheal tube 42) as needed.

Continuing to press the advancer trigger 65 to advance the endotracheal tube manipulator 45 (carrying the endotracheal tube 42) as needed until the endotracheal tube 42 is in the desired position.

Noting any halting of the advancement originating from resistance encountered and sensed by the pressure sensor (if the optional pressure sensor and advancement halting system is available).

If the optional articulation system is included, pressing the articulation actuator 66 to operate the stylet/tube articulator 64 to cause a slight bend or curve in the endotracheal tube manipulator 45 carrying the endotracheal tube 42 (used in situations where a more acute angle of the manipulator 45 carrying tube 42 is needed to manipulate the endotracheal tube 42 into position.

Positioning the endotracheal tube manipulator 45 carrying the endotracheal tube 42 in the appropriate position in the patient's airway.

Removing the tongue retractor.

Inflating the endotracheal tube 42 cuff 44.

Unlocking the endotracheal tube 42 from the endotracheal tube lock 40.

Holding the endotracheal tube 42 in place.

Pulling the endotracheal tube manipulator 45 out of the endotracheal tube 42, while leaving the bite block 53 and mouth rest 55 in place to aid in preventing biting for the duration of the intubation.

Thus the second exemplary embodiment of the endotracheal tube placement system 10' of the present invention facilitates intubation and saves times, especially for difficult intubations.

FIG. 9 illustrates a third exemplary embodiment of the endotracheal tube placement system of the present invention, generally referred to by the reference numeral 10". The endotracheal tube placement system 10" is functionally similar to the first exemplary embodiment of FIG. 1 to FIG. 6, but provides optional components. The endotracheal tube placement system 10" of the third embodiment further comprises an optional suction system 70 and a wireless video transmission system 39 (chosen from any of a variety of conventional wireless video transmission systems, as are known in the art) that is operable to transmit video data to a remote display device, such as screen display device 38. In other aspects, the endotracheal tube placement system 10" is substantially similar to the endotracheal tube placement system 10 of the first embodiment, as described above.

The optional suction system 70 comprises a port 74 disposed on the side of the endotracheal tube placement system 10, to which the clinician can connect a conventional suction tube from a grounded suction device (either wall suction or a portable suction device).

The optional suction system 70 further comprises a suction catheter 72 disposed within the endotracheal tube manipulator 45 and operatively connected to the port 74. The suction catheter 72 is configured to deliver the suction to the dital end of the endotracheal tube manipulator 45.

The optional suction system 70 additionally comprises a trigger, suction actuator 71, disposed on placement-assistive handle 20 in a location accessible to the clinician and configured to initiate and terminate the suction.

Less preferably the suction system 70 can be a self-contained suction device unit, powered by the internal power supply 23 of placement-assistive handle 20.

The addition of the suction catheter allows the clinician to clear secretions for better viewing, which may be particularly advantageous in a situation in which there is a cervical spine injury and/or bleeding in the airway.

In the third embodiment the video system 30 comprises a remote display device onto which the image transmitted from the distal end of endotracheal tube manipulator 45 is projected by cable or, more preferably, wirelessly. The remote display device is illustrated as a large screen display device 38, enabling others in the room to view the video images for assistance purposes or teaching purposes. This also facilitates digital storage of the video images, such as for teaching, review, research, or documentation. The video images may alternatively be projected to other remote display devices, such as LCD glasses worn by the clinician (not shown).

From the foregoing, it will be apparent that the endotracheal tube placement system of the present invention 10 of the current invention provides an efficient system that provides more precise control of the endotracheal tube tip, allowing guidance towards any direction by using simple, intuitive wrist movements, saving valuable time during intubation. The endotracheal tube placement system of the present invention also saves time and minimizes airway trauma by enabling simultaneous indirect visualization of the airway and introduction of the endotracheal tube 42. The ease of use, the straightforward wrist movements, and the valuable visualization of the airway during intubation reduces the learning curve and allows a wider variety of medical personnel to perform intubations. Further, the capacity to be disassembled into component parts allows the endotracheal tube placement system of the present invention to be conveniently stored or transported.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalents.

I claim:

1. An endotracheal tube placement system for use with an endotracheal tube by a clinician during intubation of a patient, comprising:
   a placement-assistive handle configured for manual turning and grasping by said clinician;
   an internal power source disposed within said placement-assistive handle;
   a semi-malleable endotracheal tube manipulator perpendicularly attached to the inner end of said placement-assistive handle and configured to receive said endotracheal tube, wherein the manual turning of said placement-assistive handle guides the distal tip of said semi-malleable endotracheal tube manipulator to achieve motion in one or more planes along the x, y and z axis;
   an endotracheal tube lock disposed at the proximal end of said endotracheal tube manipulator and configured to releasably secure said endotracheal tube to said endotracheal tube manipulator;
   a video system powered by said internal power source and comprising a display screen, a video camera disposed at the distal end of said endotracheal tube manipulator, and a light source disposed at the distal end of said endotracheal tube manipulator, wherein said video system is operable to display an image obtained from said video camera on said display screen;
   a mechanized advancer supported by said placement-assistive handle and configured to advance said endotracheal tube manipulator forward to lengthen the distance between the tip of said endotracheal tube manipulator and said placement-assistive handle; and
   an advancement halting system, wherein said advancement halting system comprises a pressure sensor operatively connected to an advancement controller, wherein said pressure sensor is operative to sense the pressure at the distal end of said endotracheal tube manipulator and said advancement controller is operative to halt the advancement of said mechanized advancer upon receipt of an unsatisfactory reading from said pressure sensor.

2. The endotracheal tube placement system, as recited in claim 1, wherein said endotracheal tube manipulator is removably attachable to said placement-assistive handle.

3. The endotracheal tube placement system, as recited in claim 2, wherein said endotracheal tube manipulator is threadingly engageable with said placement-assistive handle.

4. The endotracheal tube placement system, as recited in claim 1, wherein said display screen is removably attachable to said placement-assistive handle.

5. The endotracheal tube placement system, as recited in claim 1, further comprising an endotracheal tube stabilizer supported by said placement-assistive handle, said endotracheal tube stabilizer forming a supportive sheath configured to receive said endotracheal tube manipulator.

6. The endotracheal tube placement system, as recited in claim 5, further comprising an oral anchor attached to said endotracheal tube stabilizer, said oral anchor comprising a bite block and a mouth rest.

7. The endotracheal tube placement system, as recited in claim 1, wherein said mechanized advancer is removably attachable to said placement-assistive handle.

8. The endotracheal tube placement system, as recited in claim 1, further comprising:
   a stylet/tube articulator configured to apply pressure to a side of said endotracheal tube manipulator to increase the angle of said endotracheal tube manipulator; and
   an articulation actuator disposed on said placement-assistive handle and configured to allow said clinician to manually activate said stylet/tube articulator.

9. The endotracheal tube placement system, as recited in claim 1, further comprising an advancer trigger operatively connected to said mechanized advancer and configured to be manually operated by said clinician.

10. A method to intubate a patient with an endotracheal tube, comprising:
    placing said patient in the supine position;
    opening said patient's mouth;
    retracting the tongue of said patient to expose the oropharynx;

placing an endotracheal tube with a distal cuff onto an endotracheal tube manipulator;

locking the proximal end of said endotracheal tube onto an endotracheal tube manipulator with a endotracheal tube lock;

grasping a placement-assistive handle perpendicularly connected to said endotracheal tube manipulator carrying said endotracheal tube;

introducing said endotracheal tube carried by said endotracheal tube manipulator into the mouth of said patient;

turning said placement-assistive handle to control the movement of the distal tip of said endotracheal tube manipulator to achieve motion in one or more planes along the x, y and z axis;

viewing a display screen providing indirect visualization of the distal tip of said endotracheal tube;

advancing said endotracheal tube manipulator carrying said endotracheal tube into the airway of said patient;

positioning said endotracheal tube manipulator carrying said endotracheal tube in the appropriate location in said airway of said patient;

inflating said endotracheal tube cuff;

unlocking said endotracheal tube from said endotracheal tube lock;

retracting said endotracheal tube manipulator from said endotracheal tube positioning an oral anchor onto said patient's teeth; and using said oral anchor as a stabilization point to facilitate the control of the movement of the distal tip of said endotracheal tube manipulator.

11. The method to intubate a patient with an endotracheal tube, as recited in claim 10, wherein turning said placement-assistive handle to control the movement of the distal tip of said endotracheal tube manipulator to achieve motion in one or more planes along the x, y and z axis comprises:

moving the wrist and hand to produce a movement along the x, y, or z axis to guide said endotracheal tube manipulator carrying said endotracheal tube; and using a pushing movement to advance said endotracheal tube into the appropriate location in said airway of said patient.

12. The method to intubate a patient with an endotracheal tube, as recited in claim 10, wherein advancing said endotracheal tube manipulator carrying said endotracheal tube into the airway of said patient comprises pressing an advancer trigger to advance said endotracheal tube manipulator carrying said endotracheal tube through the mouth into the oropharynx of said patient and to the appropriate location in said airway of said patient.

13. The method to intubate a patient with an endotracheal tube, as recited in claim 10, wherein said display screen is attached to said placement-assistive handle.

14. The method to intubate a patient with an endotracheal tube, as recited in claim 10, wherein said display screen is remote from said placement-assistive handle.

15. The method to intubate a patient with an endotracheal tube, as recited in claim 10, wherein said placement-assistive handle is removably connected to said endotracheal tube manipulator.

* * * * *